United States Patent
Wang et al.

(10) Patent No.: US 10,561,647 B2
(45) Date of Patent: Feb. 18, 2020

(54) USE OF QUINOLINE DERIVATIVES FOR TREATING OESOPHAGEAL CANCER AND TREATMENT METHOD, PHARMACEUTICAL COMPOSITION AND KIT THEREOF

(71) Applicant: Chia Tai Tianqing Pharmaceutical Group Co., Ltd., Lianyungang (CN)

(72) Inventors: Xunqiang Wang, Lianyungang (CN); Ling Yang, Lianyungang (CN); Zhongnan Xu, Lianyungang (CN); Xiangjian Wang, Lianyungang (CN); Wenjun Geng, Lianyungang (CN)

(73) Assignee: Chia Tai Tianqing Pharmaceutical Group Co., Ltd., Lianyungang (CN)

( * ) Notice: Subject to any disclaimer, the term of this patent is extended or adjusted under 35 U.S.C. 154(b) by 0 days.

(21) Appl. No.: 16/068,332

(22) PCT Filed: Jan. 6, 2017

(86) PCT No.: PCT/CN2017/070352
§ 371 (c)(1),
(2) Date: Jul. 5, 2018

(87) PCT Pub. No.: WO2017/118401
PCT Pub. Date: Jul. 13, 2017

(65) Prior Publication Data
US 2019/0022082 A1    Jan. 24, 2019

(30) Foreign Application Priority Data
Jan. 8, 2016 (CN) .......................... 2016 1 0013628

(51) Int. Cl.
*A61K 31/4709* (2006.01)
*A61P 35/00* (2006.01)
(52) U.S. Cl.
CPC .......... *A61K 31/4709* (2013.01); *A61P 35/00* (2018.01)
(58) Field of Classification Search
CPC ........................... A61K 31/4709; A61P 35/00
See application file for complete search history.

(56) References Cited

U.S. PATENT DOCUMENTS

2008/0227811 A1    9/2008  Chen
2010/0075952 A1*   3/2010  ChoTang ............. C07D 487/04
                                                     514/212.06

FOREIGN PATENT DOCUMENTS

CN        101809012 A     8/2010
CN        102344438 A     2/2012
WO    WO 2015/185011 A1   12/2015

OTHER PUBLICATIONS

Lorenzen et al., "Cetuximab plus cisplatin-5-FU versus cisplatin-5-FU alone in first-line metastatic squamous cell carcinoma of the esophagus: a randomized phase II study of the Arbeitsgemeinschaft Internistische Onkologie," Annals of Oncology, Oct. 2009; 20 (10): pp. 1667-1673). (Year: 2009).*
Zhu, L.-Y. et al., "Mpact analysis of VEGF change and pathological reaction on prognosis of patients with esophageal cancer before and after radiation and chemotherapy," Anhui Medical and Pharmaceutical Journal, vol. 19, No. 1, Jan. 31, 2015, pp. 70-73 (w/English abstract, 4 pages).
International Search Report in International Patent Application No. PCT/CN2017/070352, dated Apr. 13, 2017 (w/English translation, 8 pages).
Written Opinion in International Patent Application No. PCT/CN2017/070352, dated Apr. 13, 2017 (w/English translation, 8 pages).

* cited by examiner

*Primary Examiner* — Sahar Javanmard
(74) *Attorney, Agent, or Firm* — Nixon Peabody LLP

(57) ABSTRACT

Provided in the present invention are a use of quinoline derivatives for treating oesophageal cancer and a treatment method, a pharmaceutical composition and a kit thereof. The 1-[[[4-(4-fluoro-2-methyl-1H-indole-5-yl)oxy-6-methoxy-quinoline-7-yl]oxy]methyl]cyclopropylamine provided by the present invention can effectively treat oesophageal cancer, and reduce the sum of the diameters of patient's target lesions.

15 Claims, No Drawings

USE OF QUINOLINE DERIVATIVES FOR TREATING OESOPHAGEAL CANCER AND TREATMENT METHOD, PHARMACEUTICAL COMPOSITION AND KIT THEREOF

CROSS-REFERENCE TO RELATED APPLICATIONS

The present application is a U.S. national stage of PCT/CN2017/070352 filed on Jan. 6, 2017, which claims the benefit of Chinese invention patent application No. 20161001628.4 filed on Jan. 8, 2016 in the State Intellectual Property Office of the P. R. China.

FIELD OF THE INVENTION

The present invention relates to a use of quinoline derivatives for treating oesophageal cancer, and a treatment method, a pharmaceutical composition and a kit thereof, which belongs to the technical field of medicine.

BACKGROUND OF THE INVENTION

Oesophageal cancer refers to malignant lesions formed by abnormal hyperplasia of squamous epithelium or glandular epithelium of the esophagus, and its development usually goes through the stages of epithelioid atypical hyperplasia, carcinoma in situ, infiltrating carcinoma, etc. Among them, about 90% of oesophageal cancer is squamous-cell carcinoma, and about 10% is adenocarcinoma. Oesophageal cancer involves changes of many oncogenes, tumor suppressor genes and proteins at the molecular level.

Oesophageal cancer accounts for about 2% of malignant tumors, and around the world, there are about 220 thousand oesophageal cancer patients each year. China is the high-incidence area of oesophageal cancer, and is also one of the countries with the highest mortality rate of oesophageal cancer. After diagnosed as oesophageal cancer, surgery, radiotherapy, chemotherapy and the like are often required. The treatment process will cause different levels of pain and agony to patients. Moreover, patients with distant metastases are generally unsuitable for surgery, and only palliative treatment or chemotherapy is available. Therefore, developing a drug that can effectively treat oesophageal cancer is deeply necessary.

SUMMARY OF THE INVENTION

In the first aspect, the present invention provides a method for treating oesophageal cancer, which comprises administering a therapeutically effective amount of Compound I or a pharmaceutically acceptable salt thereof to patients in need of treatment.

The chemical name of Compound I is 1-[[[4-(4-fluoro-2-methyl-1H-indol-5-yl)oxy-6-methoxyquinolin-7-yl]oxy]methyl]cyclopropylamine, and it has the following structural formula:

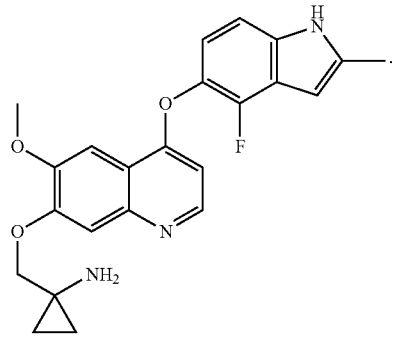

Compound I

In the second aspect, the present invention provides a use of Compound I or a pharmaceutically acceptable salt thereof in manufacturing a pharmaceutical composition for treating oesophageal cancer.

In the third aspect, the present invention provides a pharmaceutical composition for treating oesophageal cancer, which comprises Compound I or a pharmaceutically acceptable salt thereof, and at least one pharmaceutically acceptable carrier.

In the fourth aspect, the present invention provides a kit, comprising (a) a pharmaceutical composition of at least one unit dose of Compound I or a pharmaceutically acceptable salt thereof, and (b) instructions for treatment of oesophageal cancer.

In the present invention, said oesophageal cancer includes, but not limited to, esophageal squamous-cell carcinoma and esophageal adenocarcinoma.

DETAILED EMBODIMENTS OF THE INVENTION

In the first aspect, the present invention provides a method for treating oesophageal cancer, which comprises administering a therapeutically effective amount of Compound I or a pharmaceutically acceptable salt thereof to patients in need of treatment. Said oesophageal cancer includes, but not limited to, esophageal squamous-cell carcinoma and esophageal adenocarcinoma.

In some embodiments of the present invention, a method for treating esophageal squamous-cell carcinoma is provided, comprising administering a therapeutically effective amount of Compound I or a pharmaceutically acceptable salt thereof to patients in need of treatment.

In some embodiments of the present invention, a method for treating esophageal adenocarcinoma is provided, comprising administering a therapeutically effective amount of Compound I or a pharmaceutically acceptable salt thereof to patients in need of treatment.

In some embodiments of the present invention, a method for treating advanced oesophageal cancer and/or metastatic oesophageal cancer is provided, comprising administering a therapeutically effective amount of Compound I or a pharmaceutically acceptable salt thereof to patients in need of treatment.

In some embodiments of the present invention, a method for treating oesophageal cancer after failure of treatment with taxanes antitumor drugs, vinca alkaloids antitumor drugs, platinum complexes and/or pyrimidine antagonists is provided, which comprises administering a therapeutically effective amount of Compound I or a pharmaceutically acceptable salt thereof to patients in need of treatment.

In some embodiments of the present invention, taxanes antitumor drugs include, but not limited to, paclitaxel and docetaxel; vinca alkaloids antitumor drugs include, but not limited to, vinblastine, vincristine, vindesine and vinorelbine; platinum complexes include, but not limited to, miriplatin, cisplatin, carboplatin, nedaplatin and oxaliplatin; pyrimidine antagonists include, but not limited to, cytarabine, ancitabine, capecitabine, gemcitabine, fluorouracil, difuradin, doxifluridine, tegafur and carmofur.

Compound I can be administered in the free base form thereof, and can also be administered in the form of salts, hydrates and prodrugs thereof (the prodrugs will be converted into the free base form of Compound I in the body). For example, the pharmaceutically acceptable salts of Compound I are within the scope of the present invention, and the salts can be produced by different organic acids and inorganic acids in accordance with well-known processes in the art.

In some embodiments, Compound I is administered in the form of hydrochloride thereof. In some embodiments, Compound I is administered in the form of monohydrochloride thereof. In some embodiments, Compound I is administered in the form of dihydrochloride thereof. In some embodiments, Compound I is administered in the crystalline form of hydrochloride thereof. In a certain embodiment, Compound I is administered in the crystalline form of dihydrochloride thereof.

Compound I or the pharmaceutically acceptable salts thereof can be administered via various routes, including but not limited to the one selected from the following routes: orally, parenterally, intraperitoneally, intravenously, intraarterially, transdermally, sublingually, intramuscularly, rectally, transbuccally, intranasally, via inhalation, vaginally, intraocularly, via local administration, subcutaneously, intraadiposally, intraarticularly, intraperitoneally and intrathecally. In a specific embodiment, the administration is performed orally.

The administration amount of Compound I or the pharmaceutically acceptable salts thereof can be determined according to severity of diseases, response of diseases, any treatment-related toxicity, and age and health status of patients. In some embodiments, the daily administration dosage of Compound I or the pharmaceutically acceptable salts thereof is 2 mg to 20 mg. In some embodiments, the daily administration dosage of Compound I or the pharmaceutically acceptable salts thereof is 5 mg to 20 mg. In some embodiments, the daily administration dosage of Compound I or the pharmaceutically acceptable salts thereof is 8 mg to 20 mg. In some embodiments, the daily administration dosage of Compound I or the pharmaceutically acceptable salts thereof is 10 mg to 16 mg. In some embodiments, the daily administration dosage of Compound I or the pharmaceutically acceptable salts thereof is 10 mg to 14 mg. In a specific embodiment, the daily administration dosage of Compound I or the pharmaceutically acceptable salts thereof is 10 mg. In a specific embodiment, the daily administration dosage of Compound I or the pharmaceutically acceptable salts thereof is 12 mg. In a specific embodiment, the daily administration dosage of Compound I or the pharmaceutically acceptable salts thereof is 14 mg. In a specific embodiment, the daily administration dosage of Compound I or the pharmaceutically acceptable salts thereof is 16 mg.

Compound I or the pharmaceutically acceptable salts thereof can be administered one or more times daily. In some embodiments, Compound I or the pharmaceutically acceptable salts thereof is administered once per day. In some embodiments, the administration is performed once per day in the form of oral solid formulation.

Administration methods can be generally determined according to activity and toxicity of drugs, and tolerability of patients and the like. Preferably, Compound I or the pharmaceutically acceptable salts thereof is administered in the manner of interval administration. The interval administration includes administration periods and rest periods, and during the administration periods, Compound I or the pharmaceutically acceptable salts thereof can be administered one or more times daily. For example, Compound I or the pharmaceutically acceptable salts thereof is administered daily in an administration period, and then the administration is stopped for a period of time in a rest period, followed by an administration period and then a rest period, such an administration regimen can be repeated many times. Among them, the ratio of the administration period to the rest period in days is 2:0.5~5, preferably 2:0.5~3, more preferably 2:0.5~2, most preferably 2:0.5~1.

In some embodiments, the administration is continuously performed for 2 weeks and rest for 2 weeks. In some embodiments, the administration is continuously performed once daily for 14 days and rest for 14 days, followed by continuously administering once daily for 14 days and resting for 14 days, such an interval administration regimen with a two-week continuous administration period and a two-week rest period can be repeated many times.

In some embodiments, the administration is continuously performed for 2 weeks and rest for 1 week. In some embodiments, the administration is continuously performed once daily for 14 days and rest for 7 days, followed by continuously administering once daily for 14 days and resting for 7 days, such an interval administration regimen with a two-week continuous administration period and a one-week rest period can be repeated many times.

In some embodiments, the administration is continuously performed for 5 days and rest for 2 days. In some embodiments, the administration is continuously performed once daily for 5 days and rest for 2 days, followed by continuously administering once daily for 5 days and resting for 2 days, such an interval administration regimen with a five-day continuous administration period and a two-day rest period can be repeated many times.

In some embodiments, Compound I or the pharmaceutically acceptable salts thereof is separately administered to patients as the sole active ingredient.

In the second aspect, the present invention provides a use of Compound I or the pharmaceutically acceptable salts thereof in manufacturing a pharmaceutical composition for treating oesophageal cancer. Said oesophageal cancer includes, but not limited to, esophageal squamous-cell carcinoma and esophageal adenocarcinoma. In some embodiments of the present invention, a use of Compound I or the pharmaceutically acceptable salts thereof in manufacturing a pharmaceutical composition for treating esophageal squamous-cell carcinoma is provided.

In some embodiments of the present invention, a use of Compound I or the pharmaceutically acceptable salts thereof in manufacturing a pharmaceutical composition for treating esophageal adenocarcinoma is provided.

In some embodiments of the present invention, a use of Compound I or the pharmaceutically acceptable salts thereof in manufacturing a pharmaceutical composition for treating advanced oesophageal cancer and/or metastatic oesophageal cancer is provided.

In some embodiments of the present invention, a use of Compound I or the pharmaceutically acceptable salts thereof in manufacturing a pharmaceutical composition for treating oesophageal cancer after failure of treatment with taxanes antitumor drugs, vinca alkaloids antitumor drugs, platinum complexes and/or pyrimidine antagonists is provided.

In some embodiments of the present invention, taxanes antitumor drugs include, but not limited to, paclitaxel and docetaxel; vinca alkaloids antitumor drugs include, but not limited to, vinblastine, vincristine, vindesine and vinorelbine; platinum complexes include, but not limited to, miriplatin, cisplatin, carboplatin, nedaplatin and oxaliplatin; pyrimidine antagonists include, but not limited to, cytarabine, ancitabine, capecitabine, gemcitabine, fluorouracil, difuradin, doxifluridine, tegafur and carmofur.

Compound I can be administered in the free base form thereof, and can also be administered in the form of salts, hydrates and prodrugs thereof (the prodrugs will be converted into the free base form of Compound I in the body). For example, the pharmaceutically acceptable salts of Compound I are within the scope of the present invention, and the salts can be produced by different organic acids and inorganic acids in accordance with well-known processes in the art.

In some embodiments, Compound I or the pharmaceutically acceptable salts thereof is in the form of hydrochloride of Compound I. In some embodiments, Compound I or the pharmaceutically acceptable salts thereof is in the form of monohydrochloride of Compound I. In some embodiments, Compound I or the pharmaceutically acceptable salts thereof is in the form of dihydrochloride of Compound I. In some embodiments, Compound I or the pharmaceutically acceptable salts thereof is in the crystalline form of hydrochloride of Compound I. In a specific embodiment, Compound I or the pharmaceutically acceptable salts thereof is in the crystalline form of dihydrochloride of Compound I.

The amount of Compound I or the pharmaceutically acceptable salts thereof can be determined according to severity of diseases, response of diseases, any treatment-related toxicity, and age and health status of patients. In some embodiments, the daily administration dosage of Compound I or the pharmaceutically acceptable salts thereof is 2 mg to 20 mg. In some embodiments, the daily administration dosage of Compound I or the pharmaceutically acceptable salts thereof is 5 mg to 20 mg. In some embodiments, the dosage of Compound I or the pharmaceutically acceptable salts thereof is 8 mg to 20 mg. In some embodiments, the dosage of Compound I or the pharmaceutically acceptable salts thereof is 10 mg to 16 mg. In some embodiments, the dosage of Compound I or the pharmaceutically acceptable salts thereof is 10 mg to 14 mg. In a specific embodiment, the dosage of Compound I or the pharmaceutically acceptable salts thereof is 10 mg. In a specific embodiment, the dosage of Compound I or the pharmaceutically acceptable salts thereof is 12 mg. In a specific embodiment, the dosage of Compound I or the pharmaceutically acceptable salts thereof is 14 mg. In a specific embodiment, the dosage of Compound I or the pharmaceutically acceptable salts thereof is 16 mg.

In the third aspect, the present invention provides a pharmaceutical composition for treating oesophageal cancer, which comprises Compound I or the pharmaceutically acceptable salts thereof, and at least one pharmaceutically acceptable carrier. Said oesophageal cancer includes, but not limited to, esophageal squamous-cell carcinoma and esophageal adenocarcinoma.

In some embodiments of the present invention, a pharmaceutical composition for treating esophageal squamous-cell carcinoma is provided, which comprises Compound I or the pharmaceutically acceptable salts thereof, and at least one pharmaceutically acceptable carrier.

In some embodiments of the present invention, a pharmaceutical composition for treating esophageal adenocarcinoma is provided, which comprises Compound I or the pharmaceutically acceptable salts thereof, and at least one pharmaceutically acceptable carrier.

In some embodiments of the present invention, a pharmaceutical composition for treating advanced oesophageal cancer and/or metastatic oesophageal cancer is provided, which comprises Compound I or the pharmaceutically acceptable salts thereof, and at least one pharmaceutically acceptable carrier.

In some embodiments of the present invention, a pharmaceutical composition for treating oesophageal cancer after failure of treatment with taxanes antitumor drugs, vinca alkaloids antitumor drugs, platinum complexes and/or pyrimidine antagonists is provided, which comprises Compound I or the pharmaceutically acceptable salts thereof, and at least one pharmaceutically acceptable carrier.

In some embodiments of the present invention, taxanes antitumor drugs include, but not limited to, paclitaxel and docetaxel; vinca alkaloids antitumor drugs include, but not limited to, vinblastine, vincristine, vindesine and vinorelbine; platinum complexes include, but not limited to, miriplatin, cisplatin, carboplatin, nedaplatin and oxaliplatin; pyrimidine antagonists include, but not limited to, cytarabine, ancitabine, capecitabine, gemcitabine, fluorouracil, difuradin, doxifluridine, tegafur and carmofur.

Compound I can be administered in the free base form thereof, and can also be administered in the form of salts, hydrates and prodrugs thereof (the prodrugs will be converted into the free base form of Compound I in the body). For example, the pharmaceutically acceptable salts of Compound I are within the scope of the present invention, and the salts can be produced by different organic acids and inorganic acids in accordance with well-known processes in the art.

In some embodiments, Compound I or the pharmaceutically acceptable salts thereof is in the form of hydrochloride of Compound I. In some embodiments, Compound I or the pharmaceutically acceptable salts thereof is in the form of monohydrochloride of Compound I. In some embodiments, Compound I or the pharmaceutically acceptable salts thereof is in the form of dihydrochloride of Compound I. In some embodiments, Compound I or the pharmaceutically acceptable salts thereof is in the crystalline form of hydrochloride of Compound I. In a specific embodiment, Compound I or the pharmaceutically acceptable salts thereof is in the crystalline form of dihydrochloride of Compound I.

The administration amount of Compound I or the pharmaceutically acceptable salts thereof can be determined according to severity of diseases, response of diseases, any treatment-related toxicity, and age and health status of patients. In some embodiments, the daily administration dosage of Compound I or the pharmaceutically acceptable salts thereof is 2 mg to 20 mg. In some embodiments, the daily administration dosage of Compound I or the pharmaceutically acceptable salts thereof is 5 mg to 20 mg. In some embodiments, the amount of Compound I or the pharmaceutically acceptable salts thereof in the pharmaceutical composition is 8 mg to 20 mg. In some embodiments, the amount of Compound I or the pharmaceutically acceptable salts thereof is 10 mg to 16 mg. In some embodiments, the amount of Compound I or the pharmaceutically acceptable salts thereof is 10 mg to 14 mg. In a specific embodiment, the amount of Compound I or the pharmaceutically acceptable salts thereof is 10 mg. In a specific embodiment, the amount of Compound I or the pharmaceutically acceptable salts thereof is 12 mg. In a specific embodiment, the amount of Compound I or the pharmaceutically acceptable salts thereof is 14 mg. In a specific embodiment, the amount of Compound I or the pharmaceutically acceptable salts thereof is 16 mg.

In some embodiments of the present invention, the pharmaceutical compositions are the formulations suitable for oral administration, which include tablets, capsules, dusts, granulates, drip pills, pastes, powders and the like, and tablets and capsules are preferred. Among them, the tablets can be common tablets, dispersible tablets, effervescent tablets, sustained release tablets, controlled release tablets or enteric coated tablets, and the capsules can be common capsules, sustained release capsules, controlled release capsules or enteric coated capsules. The oral formulations can be prepared with well-known pharmaceutically acceptable carriers in the art by conventional methods. The pharmaceutically acceptable carriers include bulking agents, absorbing agents, wetting agents, binding agents, disintegrating agents, lubricants and the like. The bulking agents include starch, lactose, mannitol, microcrystalline cellulose or the like; the absorbing agents include calcium sulfate, calcium hydrogen phosphate, calcium carbonate or the like; the wetting agents include water, ethanol or the like; the binding agents include hydroxypropyl methylcellulose, povidone, microcrystalline cellulose or the like; the disintegrating agents include cross-linked carboxymethyl cellulose sodium, crospovidone, surfactants, low-substituted hydroxypropyl cellulose or the like; the lubricants include magnesium stearate, talc powder, polyethylene glycol, sodium dodecylsulfate, Aerosil, talc powder or the like. The pharmaceutical excipients also include colorants, sweetening agents and the like.

In one embodiment, the pharmaceutical composition is solid formulations suitable for oral administration. For example, the composition can be in the form of tablets and capsules. In a particular embodiment, the pharmaceutical composition is capsules. In a particular embodiment of the present invention, the pharmaceutically acceptable carriers of the oral solid formulations include mannitol, microcrystalline cellulose, hydroxypropyl cellulose, and magnesium stearate.

In some embodiments, a pharmaceutical composition for treating oesophageal cancer formulated as a unit dosage form is provided. In some embodiments, the pharmaceutical composition in the unit dosage form contains 2 mg-20 mg of Compound I or the pharmaceutically acceptable salts thereof. In some embodiments, the pharmaceutical composition in the unit dosage form contains 5 mg-20 mg of Compound I or the pharmaceutically acceptable salts thereof. In some embodiments, the pharmaceutical composition in the unit dosage form contains 8 mg-20 mg of Compound I or the pharmaceutically acceptable salts thereof, preferably 10 mg-16 mg of Compound I or the pharmaceutically acceptable salts thereof, and more preferably 10 mg-14 mg of Compound I or the pharmaceutically acceptable salts thereof. In a particular embodiment, the pharmaceutical composition in the unit dosage form contains 10 mg of Compound I or the pharmaceutically acceptable salts thereof. In a particular embodiment, the pharmaceutical composition in the unit dosage form contains 12 mg of Compound I or the pharmaceutically acceptable salts thereof. In a particular embodiment, the pharmaceutical composition in the unit dosage form contains 14 mg of Compound I or the pharmaceutically acceptable salts thereof. In a particular embodiment, the pharmaceutical composition in the unit dosage form contains 16 mg of Compound I or the pharmaceutically acceptable salts thereof. For example, for tablets or capsules, "a pharmaceutical composition in the unit dosage form" means each tablet or capsule.

Preferably, the pharmaceutical composition is administered in an interval administration regimen. The interval administration includes administration periods and rest periods, and during the administration periods, the pharmaceutical composition can be administered one or more times daily. For example, the pharmaceutical composition is administered daily in an administration period, and then the administration is stopped for a period of time in a rest period, followed by an administration period and then a rest period, such an administration regimen can be repeated many times. Among them, the ratio of the administration period to the rest period in days is 2:0.5-5, preferably 2:0.5-3, more preferably 2:0.5-2, and most preferably 2:0.5-1.

In some embodiments, the administration is continuously performed for 2 weeks and rest for 2 weeks. In some embodiments, the administration is continuously performed once daily for 14 days and rest for 14 days, followed by continuously administering once daily for 14 days and resting for 14 days, such an interval administration regimen with a two-week continuous administration period and a two-week rest period can be repeated many times.

In some embodiments, the administration is continuously performed for 2 weeks and rest for 1 week. In some embodiments, the administration is continuously performed once daily for 14 days and rest for 7 days, followed by continuously administering once daily for 14 days and resting for 7 days, such an interval administration regimen with a two-week continuous administration period and a one-week rest period can be repeated many times.

In some embodiments, the administration is continuously performed for 5 days and rest for 2 days. In some embodiments, the administration is continuously performed once daily for 5 days and rest for 2 days, followed by continuously administering once daily for 5 days and resting for 2 days, such an interval administration regimen with a five-day continuous administration period and a two-day rest period can be repeated many times. In some embodiments of the present invention, the oesophageal cancer is advanced oesophageal cancer and/or metastatic oesophageal cancer.

In the fourth aspect, the present invention also provides a kit, comprising (a) at least one unit dose of the pharmaceutical composition as described in the third aspect of the present invention, and (b) instructions for treatment of oesophageal cancer. In some embodiment, a kit is provided, which comprises (a) at least one unit dose of the preparation suitable for oral administration as described in the third aspect of the present invention, and (b) instructions for treatment of oesophageal cancer in the manner of interval administration. In a particular embodiment, a kit is provided, which comprises (a) at least one unit dose of tablets or capsules as described in the third aspect of the present invention, and (b) instructions for treatment of oesophageal cancer in the manner of interval administration.

In some embodiments, said oesophageal cancer includes, but not limited to, esophageal squamous-cell carcinoma and esophageal adenocarcinoma.

In some embodiments, said oesophageal cancer is advanced oesophageal cancer and/or metastatic oesophageal cancer.

In some embodiments, said oesophageal cancer is the one after failure of treatment with taxanes antitumor drugs, vinca alkaloids antitumor drugs, platinum complexes and/or pyrimidine antagonists.

In some embodiments of the present invention, taxanes antitumor drugs include, but not limited to, paclitaxel and docetaxel; vinca alkaloids antitumor drugs include, but not limited to, vinblastine, vincristine, vindesine and vinorelbine; platinum complexes include, but not limited to, miriplatin, cisplatin, carboplatin, nedaplatin and oxaliplatin; pyrimidine antagonists include, but not limited to, cytarabine, ancitabine, capecitabine, gemcitabine, fluorouracil, difuradin, doxifluridine, tegafur and carmofur.

In some embodiments, the pharmaceutical composition in the unit dosage form contains 2 mg-20 mg of Compound I or the pharmaceutically acceptable salts thereof. In some embodiments, the pharmaceutical composition in the unit dosage form contains 5 mg-20 mg of Compound I or the pharmaceutically acceptable salts thereof. In some embodiments, the pharmaceutical composition in the unit dosage form contains 8 mg-20 mg of Compound I or the pharmaceutically acceptable salts thereof, preferably 10 mg-16 mg of Compound I or the pharmaceutically acceptable salts thereof, and more preferably 10 mg-14 mg of Compound I or the pharmaceutically acceptable salts thereof. In a particular embodiment, the pharmaceutical composition in the unit dosage form contains 10 mg of Compound I or the pharmaceutically acceptable salts thereof. In a particular embodiment, the pharmaceutical composition in the unit dosage form contains 12 mg of Compound I or the pharmaceutically acceptable salts thereof. In a particular embodiment, the pharmaceutical composition in the unit dosage form contains 14 mg of Compound I or the pharmaceutically acceptable salts thereof. In a particular embodiment, the pharmaceutical composition in the unit dosage form contains 16 mg of Compound I or the pharmaceutically acceptable salts thereof. For example, for tablets or capsules, "a pharmaceutical composition in the unit dosage form" means each tablet or capsule. Herein, unless indicated otherwise, the dosages and ranges provided therein are based on the molecular weight of the free base form of Compound I.

Herein, unless indicated otherwise, qd refers to administration once daily.

Herein, the crystalline form of the hydrochloride of Compound I includes, but not limited to, crystalline Forms A, B and C disclosed in the Chinese patent application publication No. CN102344438A, wherein crystalline Forms A and B are those which do not contain crystal water and other solvents basically, and crystalline Form C is the one containing two molecules of crystal water. In some embodiments, the crystalline form of the dihydrochloride of Compound I is crystalline Form A.

Unless indicated otherwise, for the purpose of the present application, the following terms used in the Description and Claims are intended to have the meanings denoted below.

"Patients" refer to mammal, preferably human. In some embodiments, the patients are those having failed standard treatment or lacking standard treatment.

"Pharmaceutically acceptable carrier" means those which are useful in preparing a pharmaceutical composition that is generally safe, non-toxic and neither biologically nor otherwise undesirable, and that is acceptable for human pharmaceutical use when the carriers are included.

"Pharmaceutically acceptable salts" include, but not limited to acid addition salts formed from inorganic acids, such as hydrochloric acid, hydrobromic acid, sulfuric acid, nitric acid, phosphoric acid or the like; or acid addition salts formed from organic acids, such as acetic acid, trifluoroacetic acid, propionic acid, caproic acid, heptanoic acid, cyclopentane propionic acid, glycolic acid, pyruvic acid, lactic acid, malonic acid, succinic acid, malic acid, maleic acid, fumaric acid, tartaric acid, citric acid, benzoic acid, cinnamic acid, mandelic acid, methyl sulfonic acid, ethyl sulfonic acid, 1,2-ethanedisulfonic acid, 2-hydroxyethanesulphonic acid, benzenesulfonic acid, p-chlorobenzenesulfonic acid, p-toluenesulfonic acid, 3-phenylpropionic acid, trimethylacetic acid, t-butylacetic acid, dodecyl sulfuric acid, gluconic acid, glutamic acid, hydroxynaphthoic acid, salicylic acid, stearic acid and the like.

"Therapeutically effective amount" means an amount of a compound that, when administered to human for treating a disease, is sufficient to effect such treatment for the disease.

"Treatment/treating" means any administration of a therapeutically effective amount of a compound, and includes:
(1) Inhibiting the disease in a person that is experiencing or displaying the pathology or symptomatology of the disease (i.e., retarding further development of the pathology and/or symptomatology), or
(2) Ameliorating the disease in a person that is experiencing or displaying the pathology or symptomatology of the disease (i.e., reversing the pathology and/or symptomatology).

"PR" is the abbreviation of "partial response", which refers to partial remission.

"PD" is the abbreviation of "progressive disease", which refers to progression of disease.

"SD" is the abbreviation of "stable disease", which refers to stability of disease.

"Failure of Treatment" refers to intolerance of toxic and side effects, disease progression in the course of treatment, or relapse after treatment; wherein the intolerance includes, but not limited to, grade IV of hematological toxicity (grade III or more thrombocytopenia), grade III of nonhematological toxicity, or more.

"Advanced" includes "locally advanced".

EXAMPLES

Example 1 1-[[[4-(4-fluoro-2-methyl-1H-indol-5-yl)oxy-6-methoxyquinolin-7-yl]oxy]methyl]cyclopropylamine dihydrochloride (dihydrochloride of Compound I)

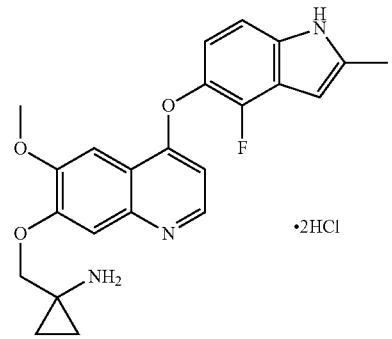 [SMILES: COc1cc2c(Oc3ccc4[nH]c(C)cc4c3F)ccnc2cc1OCC1(N)CC1]

1-[[[4-(4-fluoro-2-methyl-1H-indol-5-yl)oxy-6-methoxyquinolin-7-yl]oxy]methyl]cyclopropylamine was prepared by reference to the method of Example 24 in WO2008112407, and then the title compound was prepared by reference to the preparation method in "Examples of Salt Formation" of the Description of WO2008112407. Alternatively, the title compound was prepared by reference to the method disclosed in the Chinese patent application publication No. CN102344438A.

Example 2 Capsules Comprising 1-[[[4-(4-fluoro-2-methyl-1H-indol-5-yl)oxy-6-methoxyquinolin-7-yl]oxy]methyl]cyclopropylamine dihydrochloride (dihydrochloride of Compound I)

| Raw material/excipient names | amount (1000 capsules) |
|---|---|
| Dihydrochloride of Compound I | 14.16 g (corresponding to 12 g Compound I) |
| Mannitol | 89 g |
| Microcrystalline cellulose | 138.4 g |
| Hydroxypropyl cellulose | 5.9 g |
| Magnesium stearate | 0.99 g |

Dihydrochloride of Compound I was grinded and sifted with a 80 mesh sieve, and then mixed uniformly with mannitol and hydroxypropyl cellulose; the prescribed amount of microcrystalline cellulose was subsequently added, mixed uniformly and sifted with a 0.8 mm sieve; and finally, the prescribed amount of magnesium stearate was added and mixed uniformly, and the obtained mixture was filled into capsules. The capsule in which dihydrochloride of Compound I is at different content can be prepared by reference to the above proportion and formulation.

Example 3 Efficacy on Oesophageal Cancer

1) Medical History

A 47-year-old woman occurred dysphagia in March 2012; gastroscope results showed a semi-circle cauliflower-like mass in the esophagus at 28-31 cm from the incisors; pathology showed poorly differentiated carcinoma, squamous-cell carcinoma. In Apr. 19, 2012, CT results showed multiple nodules and masses in both lungs, wherein the larger one was about 2.9×2.1 cm; and multiple lymph nodes in the left clavicle and adjacent the esophagus, wherein the larger one was located on the left clavicle, about 3.3×3.2 cm. From Apr. 28, 2012 to September 2012, the chemotherapy regimen of paclitaxel liposome+nedaplatin+fluorouracil was performed for 6 cycles, evaluated as PR (partial remission). From September 2012 to November 2012, Tegafur/Gimeracil/Oteracil was orally administered for treatment, and the progression of the disease was found in November 2012. From Nov. 30, 2012 to Feb. 28, 2013, the chemotherapy regimen of gemcitabine+Calcium Levofolinate/fluorouracil was performed for 2 cycles, and then the chemotherapy regimen of vinorelbine+capecitabine was performed for 2 cycles, evaluated as PD (disease progression). From Mar. 19, 2013 to Apr. 19, 2013, Chinese medicine yijinsheng was used, and evaluated as PD (disease progression). From May 6, 2013 to Jun. 15, 2013, chest radiotherapy DT60G was performed without evaluation, and from Jul. 19, 2013 to February 2014, the chemotherapy regimen of docetaxel+nedaplatin/oxaliplatin was performed for 8 cycles, evaluated as PD (disease progression).

From Mar. 21, 2014, the capsules of dihydrochloride of Compound I were administered orally qd at 12 mg for treatment, and the administration was continuously performed for 2 weeks and rest for 1 week.

2) CT Results

Imageological evaluation was conducted before administration of the capsules of dihydrochloride of Compound I: the sum of the diameter of the targeted lesions was 82 mm;

Imageological evaluation was conducted at the end of the second cycle of administration of the capsules of dihydrochloride of Compound I: the sum of the diameter of the targeted lesions was 78 mm;

Imageological evaluation was conducted at the end of the sixth cycle of administration of the capsules of dihydrochloride of Compound I: the sum of the diameter of the targeted lesions was 75 mm.

3) Tolerance

The overall tolerance was good. Only I° hypercholesterolemia, I° pharyngeal pain, I° loss of appetite, I° proteinuria, I° loss of appetite, I° hand-foot skin reaction, and I° thyrotropin increase occurred occasionally.

The preferred embodiments of the invention are described in detail, but the invention is not limited to specific details in the above embodiments, and within the scope of the technical conception of the invention, a variety of simple variations of the technical solution can be carried out, all of which fall within the scope of the present invention.

It is also to be noted that the specific technical features described in the above specific embodiments can be combined in any appropriate manner without contradiction, and in order to avoid unnecessary repetition, it will not be explained separately for various possible combinations in the present invention.

In addition, various embodiments of the present invention can also be combined, as long as it does not violate the conception of the invention, which should also be regarded as the content of the invention.

What is claimed is:

1. A method for treating oesophageal cancer, comprising administering a therapeutically effective amount of Compound I or a pharmaceutically acceptable salt thereof to patients in need of treatment,

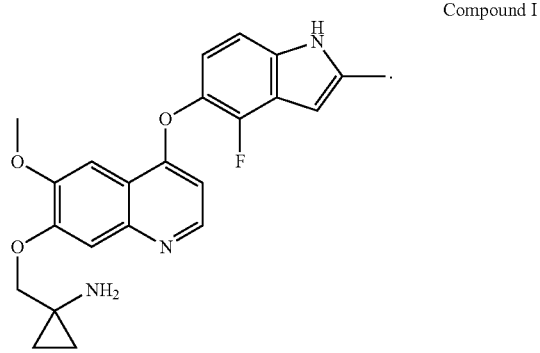 [SMILES: COc1cc2c(Oc3ccc4[nH]c(C)cc4c3F)ccnc2cc1OCC1(N)CC1]

Compound I

2. The method of claim 1, wherein the oesophageal cancer is esophageal squamous-cell carcinoma and/or esophageal adenocarcinoma.

3. The method of claim 1, wherein the oesophageal cancer is advanced oesophageal cancer and/or metastatic oesophageal cancer.

4. The method of claim 1, wherein the oesophageal cancer is the one after failure of treatment with taxanes antitumor drug, vinca alkaloids antitumor drug, platinum complex and/or pyrimidine antagonist.

5. The method of claim 1, wherein the pharmaceutically acceptable salt of Compound I is hydrochloride.

6. The method of claim 5, wherein the daily administration dosage of Compound I or the pharmaceutically acceptable salt thereof is one of the following administration dosages: 2 mg-20 mg, 5 mg-20 mg, 8 mg-20 mg, 10 mg-16 mg, 10 mg-14 mg, 10 mg, 12 mg, 14 mg and 16 mg.

7. The method of claim 5, wherein Compound I or the pharmaceutically acceptable salt thereof is administered by an interval administration regimen, and the interval administration includes administration periods and rest periods, wherein the ratio of the administration period to the rest period in days is one of the following ratios: 2:0.5-5, 2:0.5-3, 2:0.5-2, and 2:0.5-1.

8. The method of claim 3, wherein the oesophageal cancer is esophageal squamous-cell carcinoma.

9. The method of claim 4, wherein the taxanes antitumor drug is selected from paclitaxel and docetaxel; the *vinca* alkaloids antitumor drug is selected from vinblastine, vincristine, vindesine and vinorelbine; the platinum complex is selected from miriplatin, cisplatin, carboplatin, nedaplatin and oxaliplatin; and the pyrimidine antagonist is selected from cytarabine, ancitabine, capecitabine, gemcitabine, fluorouracil, difuradin, doxifluridine, tegafur and carmofur.

10. The method of claim 9, wherein the oesophageal cancer is the one after failure of treatment with paclitaxel and/or platinum complex.

11. The method of claim 1, wherein the pharmaceutically acceptable salt of Compound I is dihydrochloride.

12. The method of claim 6, wherein the daily administration dosage of Compound I or the pharmaceutically acceptable salt thereof is 12 mg.

13. The method of claim 7, wherein the ratio of the administration period to the rest period in days is 2:0.5-1.

14. The method of claim 7, wherein the interval administration regimen is one of the following regimens:

continuous administering for 2 weeks and resting for 2 weeks, continuous administering for 2 weeks and resting for 1 week, and continuous administering for 5 days and resting for 2 days, such an interval administration regimen can be repeated many times.

15. The method of claim 14, wherein the interval administration regimen is administering for 2 weeks and resting for 1 week.

* * * * *